US008865865B2

(12) United States Patent
Steinmetzer et al.

(10) Patent No.: US 8,865,865 B2
(45) Date of Patent: Oct. 21, 2014

(54) N-TERMINALLY MODIFIED TETRAPEPTIDE DERIVATIVES HAVING A C-TERMINAL ARGININE MIMETIC

(75) Inventors: Torsten Steinmetzer, Jena (DE); Gero Becker, Marburg (DE); Wolfgang Garten, Giessen (DE)

(73) Assignee: Philipps-Universitat Marburg, Marburg (DE)

( * ) Notice: Subject to any disclaimer, the term of this patent is extended or adjusted under 35 U.S.C. 154(b) by 0 days.

(21) Appl. No.: 13/126,504

(22) PCT Filed: Oct. 29, 2009

(86) PCT No.: PCT/DE2009/001514
§ 371 (c)(1),
(2), (4) Date: Sep. 8, 2011

(87) PCT Pub. No.: WO2010/048941
PCT Pub. Date: May 6, 2010

(65) Prior Publication Data

US 2011/0312873 A1 Dec. 22, 2011

(30) Foreign Application Priority Data

Oct. 29, 2008 (DE) ......................... 10 2008 053 693
Oct. 29, 2008 (DE) ......................... 10 2008 056 082
Jul. 30, 2009 (DE) ......................... 10 2009 035 593

(51) Int. Cl.
*C07K 5/10* (2006.01)
*A61K 38/07* (2006.01)
*C07K 5/083* (2006.01)
*C07K 5/09* (2006.01)
*A61K 38/00* (2006.01)

(52) U.S. Cl.
CPC ............... *C07K 5/0808* (2013.01); *A61K 38/00* (2013.01); *C07K 5/0815* (2013.01); *C07K 5/0817* (2013.01)
USPC .......................... 530/330; 514/21.9; 514/20.3

(58) Field of Classification Search
CPC .... A61K 38/00; C07K 5/0817; C07K 5/0815; C07K 5/0808
See application file for complete search history.

(56) References Cited

U.S. PATENT DOCUMENTS 5,837,218 A * 11/1998 Peers et al. .................. 424/1.69

FOREIGN PATENT DOCUMENTS

WO 2007/046781 4/2007
WO 2008/049595 5/2008

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-497.*
Bradley et al., Limits of Cooperativity in a Structurally Modular Protein: Response of the Notch Ankyrin Domain to Analogous Alanine Substitut~ons in Each Repeat, J. Mol. BloL (2002) 324, 373-386.*
Muller, Prodrug Approaches for Enhancing the Bioavailability of Drugs eith Low Solubility, Chemistry & Biodiversity, 2009, 6, pp. 2071-2083.*
Beaumont, et, al, Design of Ester Prodrugs to Enhance Oral Absorption of Poorly Permeable Compounds: Challenges to the Discovery Scientist, Current Drug Metabolism, 2003, 4, 461-485.*
Hyo-Kyung Han, Targeted Prodrug Design to Optimize Drug Delivery, AAPS Pharmsci 2000; 2 (1) article 6 pp. 1-11.*
Yashveer Singh et al, Recent Trends in Targeted Anticancer Prodrug and Conjugate Design, Curr Med Chem. 2008 ; 15(18): 1802-1826.*
Testa B., Prodrug Research: Futile or Fertile?, Biochem. Pharm., 2004, 68, pp. 2097-2106.*
Ettmayer, P. et al, Lessons Learned from Marketed and Investigational Prodrugs,J. Med. Chem., 2004, 47 (10), pp. 2393-2404.*
CBZ formula, from http://www.organic-chemistry.org/protectivegroups/amino/cbz-amino.htm, pp. 1-2, accessed Oct. 4, 2013.*
Definition of aralkyl, from http://www.merriam-webster.com/dictionary/aralkyl, p. 1, accessed Oct. 4, 2013.*
Yamamoto, Improvement of Intestinal Absorption of Peptide and Protein Drugs by Chemical Modification with Fatty Acids, Japanese Journal of Clinical Medicine, 1998, 55, pp. 49-55.*
English translation of Yamamoto, Improvement of Intestinal Absorption of Peptide and Protein Drugs by Chemical Modification with Fatty Acids, Japanese Journal of Clinical Medicine, 1998, 55, enclosed pp. 1-18.*
Carpino et al, The 9-Fluorenylmethoxycarbonyl Amino-Protecting Group, J. Org. Chem., 1972, 37, pp. 3404-3409.*
Jiao et al., "Synthetic small . . . 2,5-dideoxystreptamine", Proceedings of the National Academy of Sciences of the United States of America, Dec. 18, 2006, 103; 19707-19712.
Angliker, "Sythesis of Tight . . . Enzyme Furin", J. Med. Chem. Apr. 6, 1995, 38, 4014-4018.
Basak et al., "Inhibition of proprotein . . . their succinoyl esters", Biochem J. 1999, 338, 107-113.
Basak, "Inhibitors of proprotein convertases", J. Mol. Med. Oct. 8, 2005, 83: 844-855.
Bassi et al., "Elevated Furin . . . Cell Lines", Molecular Carcinogenesis, 31, 224-232 (2001).
Bennett et al., "A furin-like convertase . . . Alzheimer's $_{\beta}$-secretase", Additions and Corrections, The Journal of Biological Chemistry, May 4, 2000, vol. 276, p. 15561.

(Continued)

*Primary Examiner* — Julie Ha
*Assistant Examiner* — Li Ni Komatsu
(74) *Attorney, Agent, or Firm* — Clark & Brody

(57) ABSTRACT

The invention refers to multibasic, N-terminally modified tetrapeptide mimetics with a C-terminal P1-arginine mimetic, methods for their production and use for therapy and prophylaxis of diseases, caused by bacterial pathogens or viruses, as well as for therapy and prophylaxis of diabetes, arteriosclerosis, cancer, Alzheimer's or the onset of obesity, as well as the use of these compounds as inhibitors of the proprotein convertases which cleave behind basic P1 residues, especially for inhibition of the protease furin.

3 Claims, 1 Drawing Sheet

(56) References Cited

OTHER PUBLICATIONS

Figure 1A:
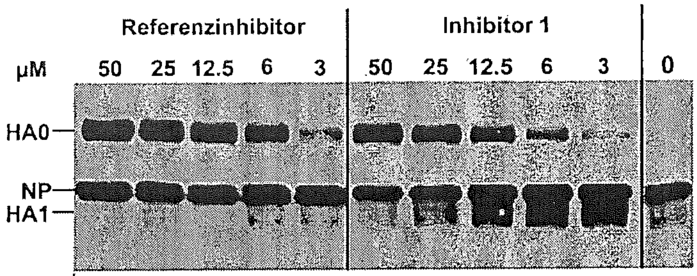

Bennett et al., "A Furin-like Convertase . . . Alzheimer's $_{\beta}$-secretase", The Journal of Biological Chemistry, Dec. 1, 2000, vol. 275, No. 48 p. 37712-37717.
Bernatowicz et al., "1*H*-Pyrazole-1-carboxamidine . . . to Peptide Synthesis", Department of Macromolecular Chemistry, Nov. 26, 1991, pp. 2497-2502.
Bontemps et al., "Potential Opportunity . . . Proprotein Convertases", Wiley InterScience (www.interscience.wiley.com), Oct. 3, 2006, Medical Research Reviews, vol. 27, No. 5, p. 631-648.
Ettmayer et al., "Lessons Learned . . . Investigational Prodrugs", Journal of Medicinal Chemistry, vol. 47, No. 10, pp. 2393-2404 May 6, 2004.
Garten et al., "Inhibition of . . . Chloroalkyl Ketones", Virology, 172, 25-31, May 2, 1989.
Hallenberger et al., "Inhibition of . . . glycoprotein gp160", Letters to Nature, vol. 360, pp. 358-361, Nov. 26, 1992.
Jean et al., "Enzymic characterization . . . GH4C1 Cells", Biochem J., 292, 891-900, 1993.
Thomas, "Furin at the . . . Embryogenesis and Disease", Nature Reviews Molecular Cell Biology, vol. 3, p. 753-766, Oct. 2002.
Kacprzak et al., "Inhibition of Furin by Polyarginine-containing Peptides", The Journal of Biological Chemistry, vol. 279, No. 35, Aug. 27, 2004, pp. 36788-36794.
Khatib et al., "Endo/exo-proteolysis . . . and metastasis", J. Mol. Med. 83: 856-864, Aug. 26, 2005.
Lila et al., "Large scale . . . Inhibitor, Melagatran", Syntheti Communications, 28(23), 4419-4429 (1998), online publication date Dec. 1, 1998, http://www.informaworld.com/smpp/title~ontent=t713597304.
Remacle, "Substrate Cleavage . . . Proprotein Convertases", J. Biol. Chem., 2008, 283, 20897-20906, Supplemental.
Schechter et al., "On the Size . . . In proteases", Biochemical and Biophysical Research Communications, vol. 27, No. 2, 1967, p. 157-162.
Schweinitz et al., "New Substrate . . . P1 Residue: Part 1", Medicinal Chemistry, 2006, 2, 349-361.
Seidah et al., "The proprotein . . . of dyslipidemia", J. Mol. Med. (2007), 85: 685-696.
Steinmetzer et al., "New Bivalent . . . at the P1-Position", Biol. Chem. vol. 381, pp. 603-610, Jul. 2000.
Steinmetzer et al., "Progress in the . . . Active Anticoagulants", Current Medicinal Chemistry, 2004, 11, 2299-2323.
Steinmetzer, "New Thrombin . . . D-CHA-PRO-Derivatives", J. Enzyme Inhibition, 1999, vol. 14, pp. 203-216.
Lin et al., "Design, Synthesis, and Biological . . . Xia as Novel Anticoagulants", XP009132450, J. Med. Chem. 2006, 49, 7781-7791.
McNaughton et al., "Resin-Bound Dynamic Combinatorial Chemistry", XP009132438, Organic Letters, 2006, vol. 8, No. 9, 1803-1806.
Steinmetzer et al., "Progress in the Development . . . Orally Active Anticoagulants", XP009132412, Current Medical Chemistry, 2004, 11, 2297-2321.
Fugere et al., "Cutting back on . . . to pharmacological inhibition" TRENDS in Pharmacological Sciences, vol. 26, No. 6, pp. 294-301, Jun. 2005.
Rockwell et al., "Precursor Processing by Kex2/Furin Proteases", XP002578946, American Chemical Society, 2002, 102, pp. 4525-4548.
Becker et al., "Potent Inhibitor of Furin . . . Decarboxylated P1 Arginine Mimetics" XP009131935, J. Med. Chem, 2010, 53, 1067-1075.
Kato et al., "Axonal transports of . . . hydrolyzing enzyme in rat sciatic nerves", NEUROCHEM Int., 32 (1998), p. 163-170.

* cited by examiner

N-TERMINALLY MODIFIED TETRAPEPTIDE DERIVATIVES HAVING A C-TERMINAL ARGININE MIMETIC

The invention refers to N-terminally modified tetrapeptide derivatives having a C-terminal arginine mimetic according to claim 1, methods for producing the tetrapeptide derivatives according to the present invention in accordance with the independent claims 18 and 23, a pharmaceutical according to claim 33 and the use of the compound according to the present invention, as well as of the pharmaceuticals according to claims 35, 36, 37 and 38.

The invention describes novel peptide mimetics which act as inhibitors of the serine protease furin and of other proprotein convertases which hydrolyze their substrates as furin C-terminally from multibasic cleavage sites. Additionally, methods for their production are provided.

Peptide mimetics are generally known. Among other functions, they serve as specific inhibitors for certain enzymes in the fields of pharmaceutics, medicine, organic chemistry and biochemistry. In doing so, every mimetic has to be designed and optimized with regard to the respective enzymatic activity which is to be influenced. As such, the effectiveness of the peptide mimetic strongly depends on the respective target enzyme.

Human proprotein convertases are part of the serine protease family. According to the current state of knowledge, there are 9 human proprotein convertases in total, of which 7 representatives (furin, PC1/3, PC2, PC4, PC5/6, PACE4 and PC7) cleave their substrates behind a basic amino acid, while two members (SKI-1 and PCSK9) hydrolyze peptide bonds behind non-basic amino acid residues (Seidah, N. G. and Prat, A., J. Mol. Med. 2007, 85, 685-696). Proprotein convertases are part of the subtilisin-like serine protease family, which differ from other serine proteases very strongly in terms of their sequence and structure, which also cleave behind basic P1 residues and to which belong, by way of example, the trypsin-like serine proteases (the designations P1, P2, P3, P4 and P5 used in the application correspond to the nomenclature proposed by Schechter and Berger for the designation of amino acid positions in protease substrates and substrate analog inhibitors, Schechter & Berger, Biochem. Biophys. Res. Comm., 1967, 27, 157).

In contrast to the trypsin-like serine proteases, it is characteristic for representatives of the proprotein convertases cleaving behind basic P1 residues to only react efficiently to substrates when these have further basic amino acid residues at the N-terminal of the cleavage site. Furin was the first representative of this group of 7 proteases to be described and is, in the meantime, also the best characterized (Thomas, G., Nat. Rev. Mol. Cell. Biol., 2002. 3, 753-766). In the case of furin, it was found that it cleaves substrates particularly efficiently when these have further basic residues in the P2 and P4 position, in addition to a basic P1 amino acid. Highly similar substrate specifies were also found for PC1/3, PC2, PC5/6 and PC7 (see MEROPS Database http://merops.sanger.ac.uk and Remade A. G. et al. J. Biol. Chem., 2008, 283, 20897-20906). However, substrates of PC4 and PACE4 also require basic residues in the P2 and P1 position.

There are numerous indications that the proteolytic effect of furin most probably causes the onset or spread of diseases. Such effects can probably be taken over in vivo by other proprotein convertases, since they have a similar substrate specificity to furin. Therefore, the explanations provided hereinafter for the physiological function of furin also apply, in principle, to the other proprotein convertases mentioned above, which cleave behind basic P1 residues.

Furin was thus described as an activator of various bacterial toxins, such as anthrax toxin, *Clostridium septicum* α toxin, *pseudomonas* exotoxin, shiga toxin, shiga-like toxins, and diptheria toxin (summarized in Thomas, G., Nat. Rev. Mol. Cell. Biol., 2002, 3, 753-766). These toxins belong to the so-called NB toxins, which contain an active domain (A) and a binding domain (B), which are both bound with each other via a furin cleavage sequence. After receptor binding of the toxins, they enter into the endosomes of the affected cells via endocytosis and are subsequently cleaved by furin, whereby these toxins can then enter into the cytosol of the cells by means of various mechanisms (Thomas, G., Nat. Rev. Mol. Cell. Biol., 2002, 3, 753-766).

A multitude of other bacterins have at least one or more toxins with a furin cleavage site, such as *Bacillus cereus, B. anthracis, B. botulinum, Clostridium perfringens, C. difficile, C. spiroforme, Bordetella pertussis, Salmonella enterica*, and several *E. coli* strains (such as *E. coli* 0157-H7), which, in the form of EHEC (enterohemorrhagic *Escherichia coli* strains), cause hemolytic colitis and hemolytic-uremic syndrome, a disease characterized by, amongst others, renal failure. *Shigella* and *E. coli* toxins are also referred to as verotoxins due to their similarity.

Furin also plays an essential role in activating various pathogenic viruses, such as in highly pathogenic avian influenza A viruses (HPAIV) (Thomas, G., Nat. Rev. Mol. Cell. Biol., 2002, 3, 753-766). They all belong to the H5 and H7 subtypes respectively, which can be distinguished from the other subtypes in a serological sense. So far, they are the only ones which have a multibasic cleavage site in their glycoprotein spike, the hemagglutinin, which is cleaved by furin and other proprotein convertases such as PC5/6. It is expected that more viruses of other subtypes will be identified in the future which have furin cleavage sites in their surface proteins. Strains belonging to these highly pathogenic avian influenza A viruses include, for example, the H5N1 virus which emerged in Hong Kong in 1997, and the H7N1 virus, which led to considerable losses in poultry stocks in the Netherlands a few years ago. The importance of furin or another proprotein convertase with similar substrate specificity for influenza also became clear, as it succeeded in generating a furin cleavage site via mutation of normally avirulent avian influenza strains, which only have a single arginine at the cleavage site (meaning that they are not usually cleaved using furin). This resulted in significantly increased virulence when all other virulence factors were available too.

Other examples of viruses with glycoproteins which can be activated via furin and other proprotein convertases include approx. 100 significant RNA and DNA viruses which lead to severe diseases in humans and numerous animal species. RNA negative-strand viruses include parainfluenza viruses, the measles virus, the mumps virus, the canine distemper virus, RSV (respiratory syncytial virus) in humans and cattle, filoviruses (the Ebola virus and Marburg virus, which cause severe haemorrhagic fevers), and the Newcastle disease virus (non classical avian influenza virus). For positive-strand RNA viruses, those types that can be activated through furin include HIV-1 (human immunodeficiency virus), HIV-2, HTLV (human T-lymphotrophic virus), and many other retroviruses, coronaviruses (e.g. the SARS coronavirus), flaviviruses (yellow fever, West Nile virus, dengue virus), which, though originally confined to limited areas, are now, as the so-called "emerging viruses", being spread across large parts of the world, predominantly in tropical areas. Early summer meningoencephalitis virus (or "tick-borne virus") is emerging in our climate zone. Other feared viruses include the Venezuelan equine encephalitis virus and the Rift Valley fever virus.

All of those viruses comprise a glycoprotein with a furin cleavage site on their surface. After cleavage of this glycoprotein via furin, a peptide sequence is unmasked, through which the viral envelope is able to merge with membranes of the virus-infected cell, thereby bringing the viral genome into the cell. Furthermore, in some viruses this fusion can result in biologically active peptides being cleaved off. Through experiments with HIV-1 and cells that have no furin, it was shown that other proprotein convertases with similar substrate specificity are also able to take over the function of furin, probably during activation.

In addition to furin-mediated effects in bacterial and viral diseases, furin or an analogous proprotein convertase may also play a role in conjunction with other diseases, and may aggravate or even activate them. As such, furin is able to cleave various pro-forms of growth factors, receptors, adhesion molecules, or matrix metalloproteinases, through which various diseases are caused. These diseases may include diabetes, arteriosclerosis, cancer/metastatic spread, but also Alzheimer's disease, and the onset of obesity (summarized in Bontemps, Y. Et al., Med. Res. Rev., 2007, 27, 631-648). For neurodegenerative diseases such as Alzheimer's, furin is potentially involved in the activation of zymogen forms of secretases, which are responsible for the creation of Aβ peptides (Bennett, B. D. et al., J. Biol. Chem. 2000, 275, 37712-37717). Due to the furin-mediated cleavage of matrix metalloproteinases, adhesion molecules, growth factors, and growth factor receptors, furin or an analogous proprotein convertase can be directly involved in the onset, development and progression of cancer, and metastatic spread, and the decomposition of extracellular matrix proteins.

It is known from the literature that furin and the furin-like proprotein convertases have important functions with regard to regulating carcinogenesis, angiogenesis, and metastatic spread. For example, these proprotein convertases cleave and activate protein precursors of growth factors, growth factor receptors, adhesion molecules, but also proforms of matrix metalloproteinases. As all these proteins are involved in the development of tumors, proprotein convertases are new targets for the development of active substances for treating cancer and metastatic spread (Bassi, D. E.; Mahloogi, H.; Al-Saleem, L.; Lopez De Cicco, R.; Ridge, J. A.; Klein-Szanto, A. J. Elevated furin expression in aggressive human head and neck tumors and tumor cell lines. Mol Carcinog 2001, 31, 224-32, Khatib, A. M.; Bassi, D.; Siegfried, G.; Klein-Szanto, A. J.; Ouafik, L. Endo/exo-proteolysis in neoplastic progression and metastasis. J Mol Med 2005, 83, 856-64).

An overview of potential substrate sequences of furin and the other proprotein convertases which require a basic amino acid as P1 residue is contained in the supplement to a recently published publication on the substrate specificity of these enzymes (supplement to Remacle A. G. et al. J. Biol. Chem., 2008, 283, 20897-20906). However, suitable inhibitors for these proteases have not been available until now, although in recent years, attempts were made by various groups to develop furin inhibitors. This also includes compounds which were derived from polyarginine peptides. Nona-D-arginine-amide, for instance, inhibits furin with an inhibition constant of 1.3 nM, while the shorter hexa-D-arginine-amide has a $K_i$ value of 7.6 nM (Kacprzak, M. M. et al., J. Biol. Chem., 2004, 279, 36788-36794). A recently published review provides an overview of known inhibitors of furin (Basak, A., J. Mol. Med., 2005, 83, 844-855). This also includes pure peptide derivatives, which derive from the prodomain of furin, but also peptidyl chloromethyl ketone (Hallenberger, S. et al., Nature, 1992, 360, 358-361), peptidyl aldehyde with C-terminal arginal (Jean, F. et al., Biochem. J., 1993, 292, 891-899), peptidyl semicarbazone and also peptides with stabilized pseudo-peptide bonds (Angliker, H., J. Med. Chem., 1995, 38, 4014-4018), with which the attempt had been made to use binding pockets on the C-terminal of the cleavage site for inhibition. Diterpene derivatives which inhibit furin in the micromolar range are also described (Basak, A. et al., Biochem. J., 1999, 338, 107-113). However, as with the other peptide derivatives with activated P1 carbonyl groups mentioned, these derivatives are not suitable for further clinical development either. The fact that these known inhibitors all have a very short half-life period in blood and a high intrinsic reactivity is particularly disadvantageous.

Therefore, the aim of the invention is to provide active substances suitable for therapeutic applications which inhibit furin or analogous proprotein convertases with high activity and specificity and are suitable for use in the treatment of diseases in which these proteases are involved. In particular, the active substances should comprise a lower intrinsic reactivity.

The inhibitors according to the current invention comprise the 5 segments P5, P4, P3, P2 and P1. Hereby, P1 is a C-terminally situated arginine mimetic, P2, P3 and P4 are amino or imino acid residues, and P5 is an N-terminal modification of the amino or imino acid residue P4. Hereby, it is advantageous if P5 is a variable structure such as an acyl, sulfonyl or alkyl residue, which is coupled to the N-terminal function of residue P4. Furthermore, the use of the inhibitors according to the present invention for the production of pharmaceuticals for the therapy and/or prophylaxis of bacterial and viral diseases is disclosed. The compounds according to the present invention are also suitable for the production of pharmaceuticals for therapy and/or prophylaxis of cancer/metastatic spread, Alzheimer's disease, arteriosclerosis, diabetes, and obesity.

Hereby, it is particularly advantageous if the compound according to the present invention is a substrate or, very particularly preferred, an inhibitor for the proprotein convertases furin, PC1/3, PC2, PC4, PC5/6, PACE4 and/or PC7. Surprisingly, it was found that N-terminally modified tetrapeptide mimetics having a C-terminal arginine mimetic according to the following formula

P5-P4-P3-P2-P1 (I)

inhibit furin highly effectively, when the P1, P2, P3, P4 and P5 residues, following the definition according to Schechter and Berger (Schechter and Berger, Biochem. Biophys. Res. Comm., 1967, 27, 157-162), have the following definitions:

P1 is selected from the following structures:

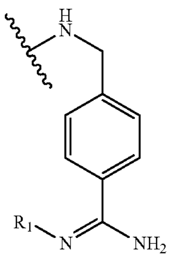

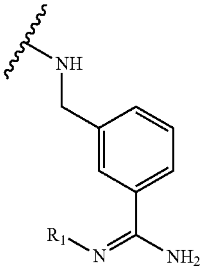

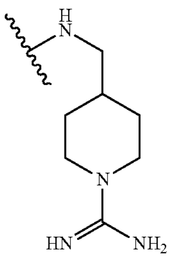

-continued

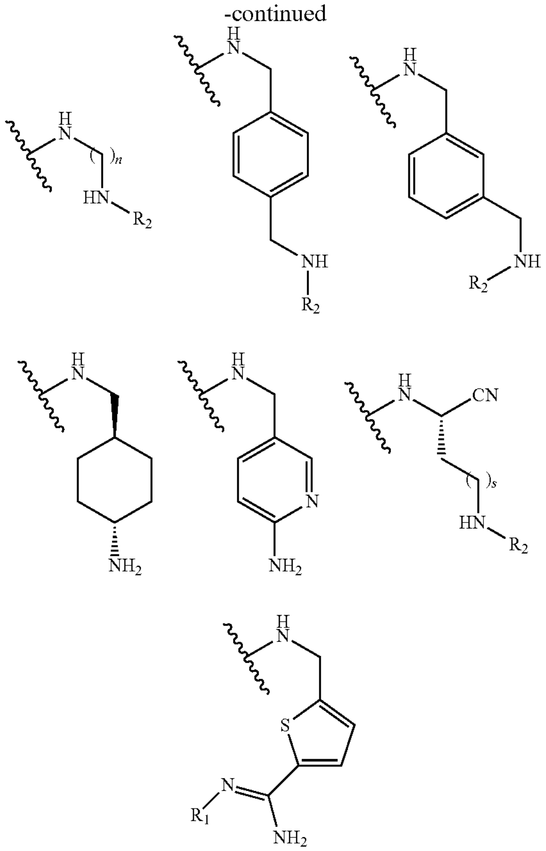

wherein $R_1$ is an H, OH, O—$CH_3$, $NH_2$, O—CO—$CH_3$ or —CO—O—$(CH_2)_m$—$CH_3$ with m being an integer from 1 to 5, and $R_2$ is an H or an amidino group

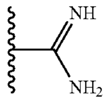

and n is equal to 3, 4 or 5, and s is equal to 2 or 3, and

P2 is an amino or imino acid selected from the following structures

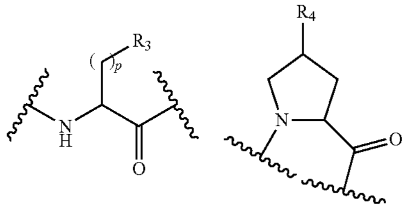

and wherein p is an integer from 0 to 5, and $R_3$ can be an amino or a guanidino group, or an O guanidino group such as in canavanine residue, or a mono- or polysubstituted or unsubstituted aryl or heteroaryl residue with 5 to 10 ring atoms, wherein the heteroaryl ring is capable of containing up to 3 heteroatoms selected from N, S, or O, wherein the substituent on the aryl or heteroaryl ring is selected from $NH_2$, $CH_2NH_2$, amidino, hydroxyamidino, guanidino, $CH_2$ guanidino, halogen, Cl, Br, I, CN, $CF_3$, alkyl with 1-3 C atoms or alkoxy with 1-3 C atoms, $COOR_5$ with $R_5$ as a hydrogen or an alkyl with 1 to 3 C atoms, and $R_4$ is an H, OH or $O(CH_2)_qR_6$ with q being an integer from 2 to 4 and $R_6$ an amino or guanidino group, and P3 is an arbitrary natural or unnatural a amino or a imino acid with L or R-configuration, and P4 is an α-amino or α-imino acid selected from the following structures

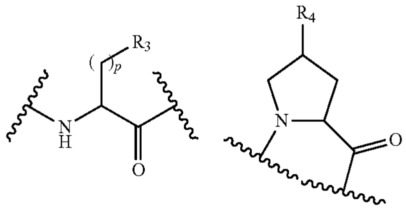

wherein p, $R_3$ and $R_4$ are defined as above, and

P5 is selected from an —H or —CO—X—$R_7$ with X being either nonexistent or equal to O or NH, wherein $R_7$ is an unsubstituted or, as the case may be, a mono- or polysubstituted, branched or unbranched, saturated or unsaturated alkyl residue with 1 to 24 C atoms and 0 to 3 double bonds, or wherein $R_7$ is an unsubstituted or (where applicable) mono- or polysubstituted aryl, heteroaryl, aralkyl, heteroaralkyl or cycloalkyl residue with 5 to 20 carbon atoms, wherein the heteroaryl ring is capable of containing up to 3 hetero atoms selected from N, S or O, wherein the one or several potentially existent substituents on $R_7$ are selected independently from each other from —$NH_2$, —$CH_2$—$NH_2$, -amidino, -hydroxyamidino, -guanidino, —$CH_2$-guanidino,-halogen, —Cl, —Br, —I, —CN, —$CF_3$, alkyl with 1-3 C atoms or alkoxy with 1-3 C atoms, —$COOR_5$ with $R_5$ as a hydrogen or alkyl group with 1 to 3 C atoms, or wherein $R_7$ represents a cholesterol residue, or a pyroglutamyl residue or another amino or imino acid residue, or an —$SO_2$—$R_7$, wherein $R_7$ is defined as above, or an unbranched or branched alkyl with 1 to 10 C atoms, wherein the alkyl residue is modified (where applicable) with a halogen, an $NH_2$, guanidino, COOH or $COOR_5$ group and $R_5$ is defined as above, or a sphingosine acylated with a bifunctional residue and, respectively, an sphingosylphosphorylcholine acylated with a bifunctional residue according to the following structures:

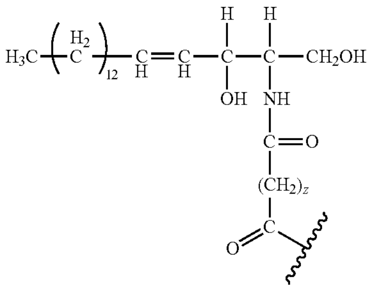

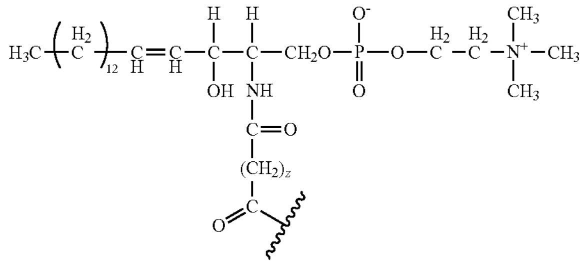

and wherein z is an integer between 2 and 20.

According to a preferred embodiment, the compounds as P1 residues according to the present invention comprise the following structures:

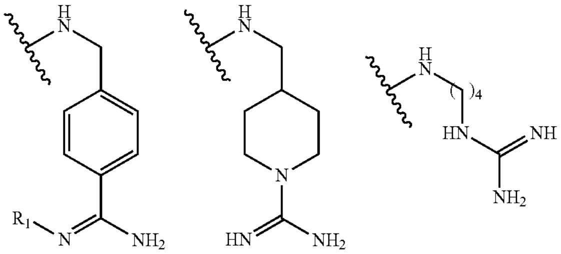

wherein $R_1$ is defined as above and wherein the 4-amidinobenzylamide derivative with a hydrogen atom is very particularly preferred as residue $R_1$. In order to achieve improved membrane permeability of the inhibitors, the hydrophobicity of the inhibitors is capable of being increased by incorporating prodrugs of the 4-amidinobenzylamide derivative (Ettmayer et al., J. Med. Chem. 2004, 47, 2393-2404), wherein the residue $R_1$ can be —OH, —O—$CH_3$, —$NH_2$, —O—CO—$CH_3$ or —CO—O—$(CH_2)_m$—$CH_3$ in these cases, with m being an integer from 1 to 5. These prodrugs are also a subject matter of the present invention. Only within the organism are they converted into inhibitorally effective compounds with a free amidino group.

It is particularly advantageous if P1 is a decarboxylated arginine mimetic. Benzamindine structures are particularly favorable. Compounds with such a P1 residue comprise a particularly low intrinsic reactivity.

The other P1 components mentioned are known arginine mimetics, which were used for the development of inhibitors of trypsin-like serine protease thrombin (see Steinmetzer and Stürzebecher review, Current Med. Chem. 2004, 11, 2299-2323). The synthesis of these components is known to persons skilled in the art.

In a further preferable practical embodiment, the P2 residue is a basic amino acid in the L-configuration. Particularly preferred are the amino acid residues arginine, lysine and their homo or nor-derivatives which have either one methylene group more or one methylene group less in the side chain. Likewise, canavanine, 3- and 4-amidinophenylalanine, as well as 3- and 4-aminomethylphenylalanine or 3- and 4-guanidinophenylalanine are preferred P2 residues, wherein also all phenylalanine derivatives mentioned, such as the homo and nor-derivatives, are also particularly suitable. Furthermore, pyridylalanine and homopyridylalanine are preferable as P2 residues, wherein the nitrogen is capable of standing in every possible position of the pyridyl ring.

In a further preferable practical embodiment, the P3 residue is an arbitrary natural or unnatural α-amino or α-imino acid residue in the L-configuration, wherein the proteinogenic amino and imino acid residues are suitable as very particularly preferred amino acid residues.

In a further preferable practical embodiment, the P4 residue is a basic amino acid in the L-configuration. Particularly suitable are the amino acid residues arginine, lysine, and their homo or nor-derivatives which have either one methylene group more or one methylene group less in the side chain. Likewise, canavanine, 3- and 4-amidinophenylalanine, 3- and 4-aminomethylphenylalanine, as well as, 3 and 4-guanidinophenylalanine, are preferred P4 residues, wherein also all phenylalanine derivatives mentioned, such as the homo and nor-derivatives, are also particularly suitable. Furthermore, pyridylalanine and homopyridylalanine are preferable as P4 residues, wherein the nitrogen is capable of standing in every possible position of the pyridyl ring.

The P5 residue is highly variable and is either suitable for being only one hydrogen atom in the simplest case or, preferably, it is a hydrophobic, saturated or (where applicable) a mono- or polyunsaturated acyl residue derived from naturally occurring fatty acids. However, aralkyl CO residue, heteroaralkyl CO residue or sulfonyl residue is also preferred, wherein all these residues are capable of being available unsubstituted (where applicable) or substituted with up to three residues. The following are particularly suitable as substituents: halogens, in particular chlorine atoms, amino groups, carboxyl groups that are also capable of being available as esters, particularly as ethyl ester, amidino, hydroxyamidino, guanidino, $CH_2$ guanidino, $CF_3$ and alkyl groups with 1-3 C atoms or alkoxy groups with 1-3 C atoms.

Particularly suitable P5 groups are the following structures:

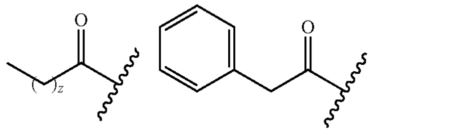

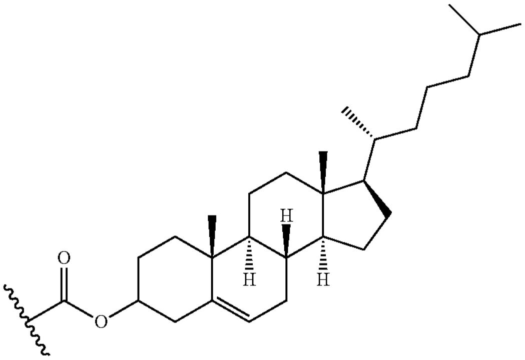

-continued

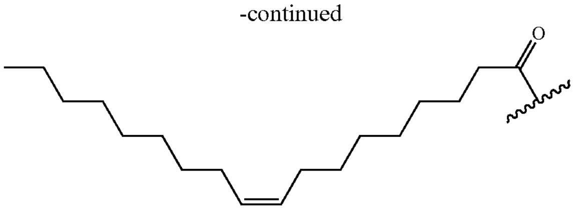

wherein z is an integer from 1 to 18, very particularly preferred z is equal to 8, 14 or 16 and also with a bifunctional residue of acylated sphingosine or, respectively, with a bifunctional residue of acylated sphingosylphosphorylcholine having the following structures:

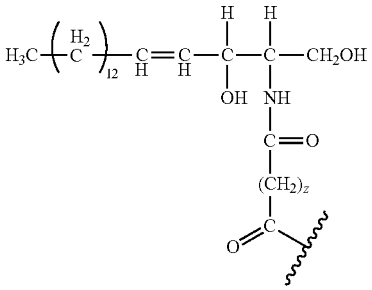

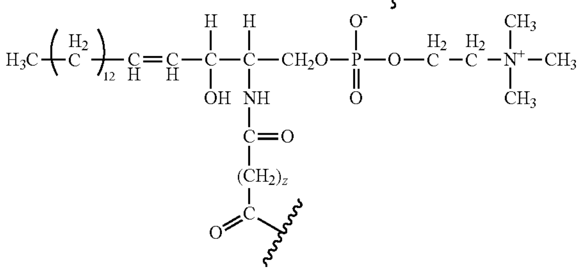

and wherein z is an integer between 2 and 20.

Methods for the synthesis of the compounds described are another subject matter of the invention, wherein synthesis is possible through the combination of solid phase and solution syntheses or through pure solution syntheses.

The following steps are carried out during synthesis of a compound according to the general formula (I) through the combination of solid phase and solution syntheses:

Synthesis of the segment P5-P4-P3-P2 through solid phase peptide synthesis, for example on a 2-chlorotrityl chloride resin according to standard procedures of Fmoc chemistry, subsequent cleaving of the peptide segment from the resin under suitable acidic conditions, wherein side chain protecting groups are either retained or cleaved off, coupling of a suitable P1 component by means of racemization-free standard methods, which can be present in a protected, if appropriate, or unprotected manner, and, as the case may be, cleavage of all protecting groups which may still be present, including for example treatment with corresponding acids, e.g. with trifluoroacetic acid, HBr in glacial acetic acid, HCl in glacial acetic acid, HF, trifluoromethanesulfonic acid, wherein the acids can possibly still contain scavengers, e.g. water, triisopropylsilane, anisole, dimethyl sulfide or other known scavengers with free mercapto groups, other existing protecting groups will (where applicable) be removed through catalytic hydration with hydrogen and palladium deposited on activated carbon as a catalyst, and final purification through crystallization, chromatography, preferably reversed-phase chromatography or ion exchange chromatography or through countercurrent distribution, and where applicable, conversion into another, or respectively more suitable, salt form.

Alternatively, for the synthesis of compounds with a C-terminal agmatine residue for example, a trityl chloride resin is charged with 1,4-diaminobutane according to standard methods and the remaining components P2, P3, P4 are consecutively coupled through Fmoc chemistry, and P5 according to standard methods. The cleavage of the peptide from the resin is carried out with suitable acids or acid-containing cleavage cocktails, wherein either all protecting groups are removed, however, certain protecting groups such as in the side chain of lysine are retained, followed by the final composition of the guanidino group by reaction of amino groups with pyrazole carboxamidine×HCl and DIPEA either in DMF or, where applicable, also in organically aqueous solvents comprising sodium carbonate or in pure aqueous sodium carbonate solution (Bernatowicz, M. S. et al., J. Org. Chem., 1992, 57, 2497-2502). Analogously, any other diamines are suitable for being used for loading the tritylchloride resin. If, at the end, the reaction with pyrazole carboxamidine is omitted, compounds are obtained with a C-terminal amino group.

For syntheses on a larger scale ("upscaling"), those methods with which only pure solution synthesis steps are applied are particularly suitable. Solution peptide synthesis usually begins with a suitable C-terminal P1 component, to which the subsequent Nα-urethane and, if necessary, also side chain protected P2 component is coupled, followed by cleavage of the Nα-urethane protecting group and the coupling of the subsequent Nα-urethane protected residue. If necessary, all intermediates occurring during synthesis can be purified. The BOC protecting group is particularly suitable as Nα-urethane protecting group. Synthesis is completed analogously; in the final steps, the P5 component is coupled and all protecting groups are subsequently removed. By means of this pure solution synthesis strategy, racemizations, which frequently cause a problem in segment couplings, as they may occur during the above mentioned combined solid phase and solution synthesis, may be minimized during coupling steps. By way of example, solution synthesis comprises the following steps:

a) Synthesis of a P1 component which is suitably protected on the terminal amidino or guanidino group with a free amino group, either available as salt or free base, e.g. of the following compound:

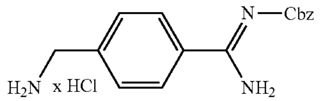

(described in Lila et al., Synth. Commun., 1998, 28, 4419-4429)

b) Coupling of a Nα-BOC or an otherwise suitably Nα-urethane protected amino or imino acid with a suitable side chain protecting group, if necessary, to the free amino group of the P1 component, wherein all suitable binding methods used in peptide chemistry with known auxiliary bases are suitable for use. This comprises the mixed anhydride method, carbodiimide method, active ester method, azide method, propane phosphonic acid anhydride method, or coupling with Triazimoch, TBTU, HBTU, BOP, PyBOP, HATU or other binding regents based on uronium or phosphonium salts, followed by processing the reaction mixture through known purification and crystallization methods, and (where applicable) followed by a chromatography step for purification purposes, and followed by standard cleavage of the Nα-protecting group, wherein the P2-P1 segment with a free amino group on the P2 component is obtained. As such, for the cleavage of the Nα-BOC protecting group for example, trifluoroacetic acid or HCl in a suitable organic solvent such as ethyl acetate, acetic acid, diethyl ether or dioxane is normally used, c) Coupling of an Nα-BOC or otherwise suitably Nα-urethane protected P3 amino or imino acid to the free amino group of the P2-P1 segment from step b) analogously to the methods described in step b), followed by processing the reaction mixture as described in step b) and the cleavage of the Nα-protecting group, wherein the P3-P2-P1 segment is obtained with a free N-terminal amino group on the P3 residue as described in step b), d) Coupling of an Nα-BOC or otherwise suitably Nα-urethane protected P4 amino or imino acid to the free amino group of the P3-P2-P1 segment from step c) analogously to the methods described in step b), followed by the processing of the reaction mixture described in step b) and the cleavage of the Nα-protecting group, wherein the P4-P3-P2-P1 segment is obtained with a free N-terminal amino group on the P4 residue as described in step b), e) Coupling of the P5 residue to the free amino group of the P4-P3-P2-P1 segment from step d), analogously (where applicable) to the methods described in step b), or coupling of a P5 component which is already available as an acid chloride or active ester, especially as a succinimide ester, in the presence of auxiliary bases without a further coupling reagent.

f) Cleavage of all protecting groups still present by conventional methods comprising, for example, catalytic hydrogenation with hydrogen and palladium deposited on activated carbon as a catalyst, or treatment with corresponding acids such as trifluoroacetic acid, HBr in glacial acetic acid, HCl in glacial acetic acid, HF, trifluoromethanesulfonic acid, wherein the acids can possibly still contain scavengers e.g. water, triisopropylsilane, anisole, dimethyl sulfide or other established scavengers with free mercapto groups, and g) final purification through crystallization, chromatography, preferably reversed-phase chromatography or ion exchange chromatography or through countercurrent distribution, and h) where applicable, conversion into another, or respectively more suitable, salt form.

Methods for carrying out couplings of segments in solution are also a subject matter of the invention, wherein racemization-free methods in particular, such as azide coupling in which a suitable N-terminal and side chain protected peptide methyl ester is converted by reaction into hydrazide, from which the azide, which is used for the coupling to a component or a segment with a free amino group, is then produced through standard procedures, are used for such couplings of segments. On the other hand, other coupling methods are also suitable for use, wherein, in particular, weak auxiliary bases such as collidine are used, or suitable additives such as 6-Cl—HOBt or HOAt are applied.

For the aforementioned methods, all known peptide chemistry synthesis methods, including all amino acid derivatives with suitable protecting groups, suitable binding reagents, and suitable cleaving reagents in corresponding solvents are suitable for use. These methods are described in detail in standard works focusing on peptide chemistry and organic chemistry (Houben-Wely Volume E22, Synthesis of Peptides).

Pharmaceutically suitable, or respectively acceptable salts are another subject matter of the invention. These salts have to comprise a pharmaceutically acceptable anion or cation. Suitable pharmaceutically acceptable acid addition salts for the compounds according to the present invention include salts of inorganic acids, such as hydrochloric acid, hydrogen bromide, phosphorous, methaphosphorous, saltpeter, sulfone and sulfuric acid, or organic acids such as acetic, benzyl sulfonic, benzoic, citric acid, ethanesulfonic, fumaric, gluconic, glycolic, isethionic, lactic, lactobionic, maleic, methane sulfonic, succinic, p-Toluenesulfonic, tartaric, and trifluoroacetic acid. For medicinal purposes, the use of chloride or acetate salt is particularly preferred. Suitable pharmaceutically acceptable basic salts are e.g. ammonium salts, alkali metal salts (such as sodium and potassium salts), and alkaline earth salts (such as magnesium and calcium salts).

Salts with a non-pharmaceutically acceptable anion likewise belong to the scope of the invention as useful intermediate products for the production or purification of pharmaceutically acceptable salts and/or for use in non-therapeutic applications, e.g. in vitro.

The term "physiological functional derivative" used hereinafter refers to every physiologically acceptable derivative of a formula (I) compound according to the present invention, e.g. an ester that is in a position (either directly or indirectly) to form a formula (I) compound or an active metabolite of this compound during the ester's administration to a mammal such as a human. Physiologically functional derivatives include prodrugs of the compound according to the present invention. Such prodrugs are capable of being metabolized in vivo to a compound according to the present invention. These prodrugs may themselves either be effective or not. Suitable prodrugs for benzamidine groups are, for example, compounds for which amidine is available as hydroxyamidine, methoxyamidine, acetylhydroxyamidine, or in particular as ethyloxycarbonylamidine or hexyloxycarbonylamidine (Ettmayer. et al., J. Med. Chem. 2004, 47, 2393-2404).

The compounds according to the present invention may also be available in various stereoisomeric forms as well as in polymorphic forms, e.g. as amorphous and crystalline polymorphous forms.

All subsequent references refer to compounds according to formula (I) as described above, as well as to their salts, solvates and physiologically functional derivatives.

The present invention also refers to the use of formula (I) compounds as pharmaceuticals for the treatment and prophylaxis of bacterial and viral diseases such as diabetes, arteriosclerosis, cancer/metastatic spread, Alzheimer's or the onset of obesity, in which furin or analogous proprotein convertases cleaving behind basic P1 residues are involved. A pharmaceutical composition containing a formula (I) compound is also a subject matter of this invention. The amount of the compound according to formula (I) required to achieve the desired biological effect depends on a series of factors, e.g. the specific compound chosen, the intended use, the type of administration and the clinical condition of the patient. For the prophylaxis or therapy of the conditions mentioned above, the compounds according to formula (I) are themselves suitable for use as a compound. However, it is preferred that they are available with a carrier, or auxiliary, in the form of a pharmaceutical composition. The carrier or auxiliary, respectively, has to be naturally acceptable in the sense that it is compatible with the other constituent parts of the composition and not harmful to the patient's health.

The carrier is capable of being a solid, a liquid or both and is preferably formulated with the compound as a single dose, for example as a tablet, which may contain 0.05 wt-% to 95 wt-% of the active substance. Further pharmaceutically active substances may also be available, including further compounds according to formula (I). The pharmaceutical compositions according to the present invention are suitable for being produced according to one of the known pharmaceutical methods which essentially consist in mixing the constituent parts with pharmaceutically acceptable carriers and/or auxiliaries.

Pharmaceutical compositions according to the present invention are, in particular, those that are suitable for oral, rectal, topical, peroral (e.g. sublingual), and parental (e.g. subcutaneous, intramuscular, intradermal or intravenous) administration, although the most suitable means of administration in each individual case depends on the type and severity of the condition to be treated and the type of formula (I) compound used in each case. Aerosols are also suitable pharmaceutical compositions for the compounds according to the present invention, which are also suitable in the form of aerosol sprays, particularly for the treatment and prophylaxis of diseases relating to the respiratory tract. Coated formulations and coated delayed-release formulations are also included in the scope of the invention. Preferable are acid- and gastric acid-resistant formulations. Suitable gastric acid-resistant coatings comprise cellulose acetate phthalate, polyvinyl acetate phthalate, hydroxypropyl methylcellulose phthalate and anionic polymers from methacrylic acid and methacrylic acid methyl ester.

Suitable pharmaceutical compounds for oral administration can be present in separate units such as capsules, cachets, lozenges, or tablets, which in each case contain a specific amount of the compound according to formula (I); as powder or granules; as a solution or suspension in an aqueous or non-aqueous liquid; or as an oil-in-water or water-in-oil emulsion. As already mentioned, these compositions can be prepared according to any suitable pharmaceutical method that comprises a step in which the active substance and carrier (potentially comprising one or more additional constituent parts) are brought into contact. In general, the compositions are produced through equal and homogenous mixing of the active substance with a liquid and/or finely distributed solid carrier, after which the product, if necessary, is shaped.

By way of example, a tablet can thus be prepared by pressing or shaping a powder or granules of the compound, if appropriate with one or more additional constituent parts. Pressed tablets can be produced by tableting the compound in a free-flowing form such as, for example, a powder or granules, and, if appropriate, mixed with a binding agent, lubricant, inert diluent and/or one or several surfactants/dispersants in a suitable machine. Shaped tablets can be produced by shaping the pulverulent compound moistened with an inert liquid diluent in a suitable machine.

Pharmaceutical compositions suitable for peroral (sublingual) administration comprise lozenges, which contain a compound according to formula (I) with a flavoring agent, normally sucrose, gum Arabic or tragacanth, and pastilles, which comprise the administration of an inert base such as gelatin and glycerin or sucrose and gum Arabic.

Suitable pharmaceutical compositions for parental administration preferably comprise sterile aqueous preparations of a compound according to formula (I), which are preferably isotonic with the blood of the intended recipient. These preparations are preferably administered intravenously, though subcutaneous, intramuscular or intradermal administration via injection is also suitable.

These preparations are especially suitable for being produced by mixing the compound with water and rendering the solution obtained sterile and isotonic with the blood. Injectable compositions according to the present invention generally contain 0.1 to 5 wt.-% of the active compound.

As regards further formulations, refer to known manuals.

The invention also concerns methods for the production of pharmaceutical compositions, in which one or more compounds according to the general formula (I) are mixed with suitable carriers and auxiliaries (see above).

It is particularly advantageous for the compound according to the present invention or a pharmaceutical according to the present invention to be suitable for use for the therapy or prophylaxis of a disease caused by a virus or bacteria as well as for the therapy and prophylaxis of diabetes, arteriosclerosis, cancer, Alzheimer's or obesity, in particular in oral, subcutaneous, intravenous, or transdermal form or in the form of a spray for the treatment of diseases in the respiratory tract.

Hereby, it is advantageous for the compound according to the present invention or a pharmaceutical according to the present invention to be used for the therapy or prophylaxis of diseases caused by bacterial pathogens, in particular caused by pathogens from the group *Pseudomonas* spec., *Shigella* spec., *Corynebacterium diphtheriae, Bacillus cereus, Bacillus anthracis, Bacillus butulinus, Clostridium perfringens, Clostridium difficile, Clostridium septicum, Clostridium spiroforme, Bordetella pertussis, Salmonella enterica*, or through selected *Escherichia coli* strains, in particular *E. coli* strains that cause hemolytic colitis, hemolytic uremic syndrome and/or renal failure, more especially *E. coli* 0157-H7.

For the therapy or prophylaxis of diseases caused by viruses, the compound or pharmaceutical is suitable for use particularly in diseases caused by viruses of the following group:

- Highly pathogenic avian influenza A viruses, predominantly the H5 and H7 subtypes respectively,
- RNA negative strand viruses such as parainfluenza viruses, the measles virus, the mumps virus, the canine distemper virus, respiratory syncytial virus, filoviruses such as the Ebola virus and the Marburg virus, and the Newcastle disease virus, as well as
- Positive-strand RNA viruses such as HIV-1, HIV-2, HTLV and other retroviruses, in particular coronaviruses such as the SARS coronavirus, flaviviruses, yellow fever viruses, the West Nile virus, the dengue virus, or the early summer meningoencephalitis virus, the Venezuelan equine encephalitis virus or the Rift Valley fever virus.

It is recognizable that the compound according to the present invention or the pharmaceutical according to the present invention is suitable for being used very particularly advantageously for the inhibition of the proprotein convertases furin, PC1/3, PC2, PC4, PC5/6, PACE4, and/or PC7.

Figure 1B:
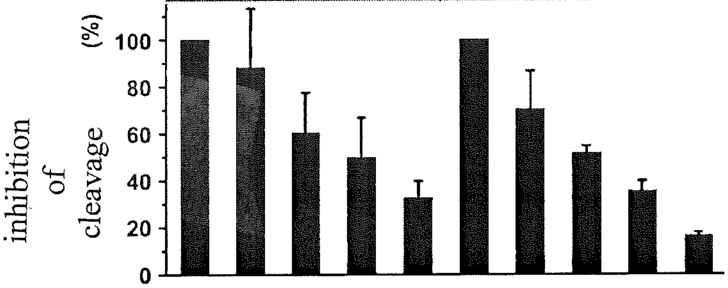

Further characteristics, details and advantages of the invention result from the text of the claims, as well as from the following description of embodiments through the figures. The figures show:

FIG. 1A shows the inhibition of HA cleavage of the avian influenza virus through different concentrations of inhibitor 1 (Phac-Arq-Val-Arg-4-amidinobenzylamide×3 TFA) and of reference inhibitor dec-Arg-Val-Lys-Arg-CMK FIG. 1B The statistical evaluation of the Western blotting shown in FIG. 1A is represented in illustration of FIG. 1B, with the bars in FIG. 1B corresponding to the lanes shown in FIG. 1A.

Figure 2:
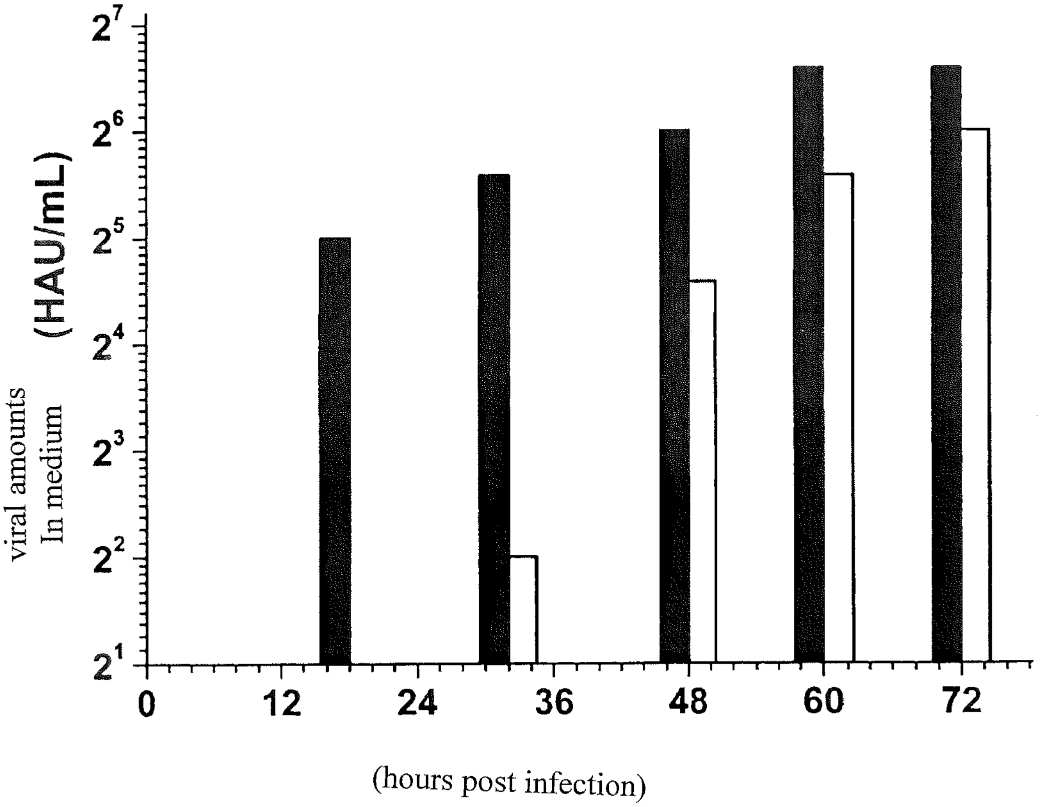

FIG. 2 the multi-cycle reproduction of FPV in cell culture in the presence of inhibitor 1 and without inhibitor.

A detailed description of the figures can be found in the description of examples 7 and 8.

PRACTICAL EMBODIMENTS

Methods for the Analysis of the Compounds

Analytical HPLC

For the analytical reversed-phase HPLC, the following was used: an HPLC system (model LC-10A) from the company Shimadzu, consisting of the sub-systems CTO-10A column heater, LC-10Tvp pumps (2×), DGU-14A degasser, SIL-10Axl auto-injector, SCL-10Avp system controller, SPD-M10Avp photo diode array detector, and a column 250/4,6 Nucleodur 100-5 C18 ec from the company Macherey-Nagel (Düren, Germany) utilizing the corresponding software Shimadzu CLASS-VP, Version 7.2.1. Detection took place at 220 nm. Water with 0.1% TFA (A) and acetonitrile with 0.1% TFA (B) at a flow rate of 1 mL/min and a linear gradient (increase of 1% B/min) served as eluents. The respective start conditions (% B) are indicated with the syntheses.

Preparative HPLC

For the preparative RP-HPLC, an HPLC system from the company Varian was used, consisting of the sub-systems Varian PrepStar Model 281 preparative pumps (1×), Varian ProStar Model 320 UV-Vis Detector, Varian Fraction Collector Model 701, and a column VP 250/32 Nucleodur 100-5 C18 ec from the company Macherey-Nagel (Düren, Germany), utilizing the corresponding Star-Software V. 6.0. Detection took place at 220 nm. Water with 0.1% TFA (A) and acetonitrile with 0.1% TFA (B) at a flow rate of 20 mL/min and a suitable gradient likewise served as eluents.

Mass Spectroscopy

The spectra were taken using an instrument from the company Applied Biosystems (Qtrap 2000) or a spectrometer of the Autospec type from the company Micromass.

Thin-Layer Chromatography

For the thin-layer chromatography, silica gel plates Adamant $UV_{254}$ from the company Macherey Nagel were used. A mixture of n-butanol, glacial acetic acid and water (4:1:1) served as mobile phase. The detection of compounds took place through UV absorption at 254 nm. Furthermore, a ninhydrin solution (300 mg ninhydrin dissolved in 100 mL n-butanol and 3 mL glacial acetic acid) and, following incubation of the TLC plate in a chlorine atmosphere, an o-tolidine solution (150 mg o-tolidine and 2.1 g KI dissolved in 2 mL glacial acetic acid and 148 mL water) was used for detection purposes.

NMR

The $^1H$ and $^{13}C$-NMR spectra were taken with an NMR spectrometer of type ECX-400 from the company Jeol Inc. USA ($^1H$-NMR: 400 MHz, $^{13}C$-NMR: 100 MHz). The samples were dissolved in commercially available deuterated solvents of standard commercial qualities. The chemical displacements were provided as 6 values in parts per million (ppm). The solvent signals were used as a reference.

LIST OF ABBREVIATIONS USED

Ac acetyl
Amb amidobenzyl
Boc tert.-butyloxycarbonyl
Bzl benzyl
Cbz benzyloxycarbonyl
DIPEA diisopropylethylamine
DCM dichloromethane
DMF N,N-dimethylformamide
Fmoc fluorenylmethyloxycarbonyl
hArg homoarginine
HBTU O-benzotriazole N,N,N',N'-tetramethyluronium hexafluorophosphate
HPLC High-performance liquid chromatography
MS mass spectroscopy
NMM N-methylmorpholine
NMP N-methylpyrrolidone
NMR nuclear magnetic resonance spectroscopy
Phac phenylacetyl
PyBOP benzotriazol-1-yl-N-oxy-tris(pyrrolidino)phosphonium hexafluorophosphate
PyBrOP bromo-tris-pyrrolidino-phosphonium-hexafluorophosphate
RT room temperature
tBu tert.-butyl
TFA trifluoroacetic acid
Tfa trifluoroacetyl
THF tetrahydrofurane All Fmoc amino acids, resins, coupling reagents and other reagents used for synthesis were procured from the companies Orpegen, Iris Biotech, Novabiochem, Bachem, Aldrich, Fluka and Acros.

PRACTICAL EMBODIMENT 1

Phac-Arg-Val-Arg-4-amidinobenzylamide×3 TFA=Inhibitor 1

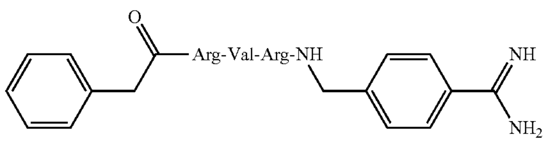

x3 TFA or, respectively, in detailed structure

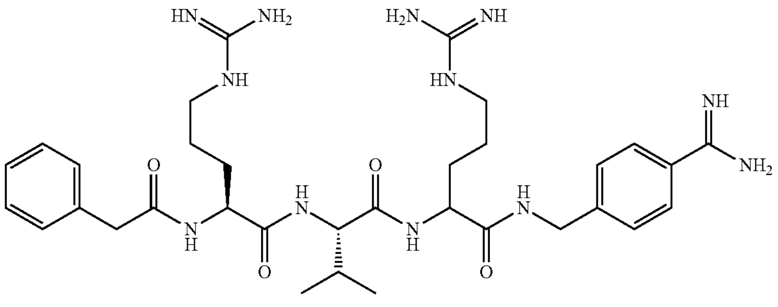

3 x$F_3C$—COOH (hereinafter, the standard amino acids will always be referred to in three-letter code).

Step a) 4-amidinobenzylamine×2 HCl

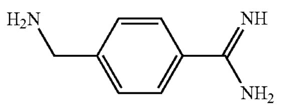

x2 HCl 10 g (32.5 mmol) Boc-4-acetylhydroxyamidinobenzylamide (produced analogously to Schweinitz, A. et al., Med. Chem., 2006, 2, 349-361) was dissolved in 300 mL of 90% acetic acid, treated with 650 mg catalyst (10% Pd/C) and hydrogenated for 6 h at about 35 C and for 36 h at RT with hydrogen. The catalyst was removed by filtration and the solvent was removed in vacuo. The remainder was dissolved in 150 mL water, treated with 40 mL concentrated HCl and stirred for 1.5 h. The solution was concentrated in vacuo, the residue dissolved in water again, and the solvent concentrated in vacuo Renewed dissolving in water and lyophilization yields the product (whitish solid, 6.8 g (30.6 mmol)).

$^1$H-NMR (400 MHz, $D_2O$): δ [ppm]=4.46 (s, 2H, H-1), 7.80-8.01 (2d, 4H, arom.).

$^{13}$C-NMR (100 Mhz, $D_2O$): δ [ppm]=42.64 (2H, H-1), 128.65 (2H, H-3), 129.26 (1H, H-5), 129.61 (2H, H-4), 138.69 (1H, H-2), 166.47 (1H, H-6).

Step b) Phac-Arg(Pbf)-Val-Arg(Pbf)-OH

The loading of 2-chlorotrityl chloride resin (1.5 g) with Fmoc-Arg(Pbf)-OH was carried out in a glass container with fritted base according to the standard procedure of the producer with equimolar amounts of Fmoc-Arg(Pbf)-OH (1.51 g, 2.325 mmol) and 4 eq. DIPEA (9.3 mmol, 1.55 mL) in relation to the stated resin loading (1.55 mmol/g) in dry DCM over a time period of 2 h. Thereafter, the reaction solution was removed, the resin washed and dried 3× with DCM/methanol/DIPEA (85/10/5 (v/v)), 3× with DCM, 2× with DMF and 2× with DCM. Subsequently, the remaining components were manually coupled by means of a standard Fmoc-synthesis protocol, wherein in the last step, phenylacetic acid was used in place of a Fmoc-amino acid. After the end of synthesis, the resin was washed several times with DMF and DCM. The cleavage from the resin was carried out with 1% TFA in DCM (v/v) in 30 min under shaking. The cleaving solution was pressed out and concentrated in vacuo, subsequently, the cleavage from the resin was repeated 2× under identical conditions. The product was lyophilized with 80% tert.butanol and used directly for the next step in the synthesis (white powder, HPLC: start at 30% B, elution at 35.57 min, MS calcd. 1051.5, MS found 1074.3 $(M+Na)^+$).

Step c) Phac-Arg-Val-Arg-4-amidinobenzylamide×3 TFA=Inhibitor 1

105 mg (0.1 mmol) Phac-Arg(Pbf)-Val-Arg(Pbf)-OH as raw product, 50.9 mg (0.3 mmol) 6-Cl—HOBt, 23 mg (0.1 mmol) 4-amidinobenzylamide×2 HCl and 57.3 mg (0.11 mmol) PyBOP were dissolved in 500 μL DMF and treated with 51.4 μL (0.3 mmol) DIPEA. The assay was stirred for 2 h at RT. The solvent was removed in vacuo and the oily remainder was charged with 2 mL of a mixture of 95% TFA, 2.5% triisopropylsilane and 2.5% water (v/v). After 3 h of shaking at RT, the product was precipitated out through addition of diethyl ether, removed by centrifugation and the precipitate washed 2× with diethyl ether. Purification was carried out through preparative HPLC; the product-containing fractions were combined and lyophilized (white powder 60 mg, (HPLC: start at 1% B, elution at 24.17 min, MS calcd. 678.4, MS found 679.4 $(M+H)^+$).

PRACTICAL EMBODIMENT 2

Phac-Arg-Val-Arg-agmatine×3 TFA=inhibitor 2

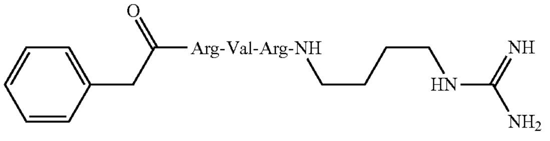

x3 TFA

Step a) Phac-Arg-Val-Arg-NH—$(CH_2)_4$—$NH_2$×3 TFA=Inhibitor 2a 100 mg trityl chloride resin was loaded with a 4-fold excess of 1,4-diaminobutane (0.6 mmol) in relation to the stated resin loading (1.5 mmol/g) of the producer in the reaction vessels of the peptide synthesis machine (Syro 2000, Multisyntech GmbH, Witten, Germany) with dry THF as solvent over a time period of 2 h. Thereafter, the solvent was removed, and the resin was washed 3× with DCM/methanol/DIPEA (85/10/5 (v/v)), 3× with DCM, 2× with DMF and 2× with DCM.

The following synthesis steps were carried out by means of a multiple peptide synthesis machine according to a standard Fmoc protocol in DMF/NMP with double coupling and, respectively, 4-fold excesses of Fmoc amino acid, HOBt, and HBTU in the presence of 8 equivalents of DIPEA. For cleavage of the Fmoc, a mixture of piperidine/DMF/NMP (1:1:1), respectively, was used. In the last synthesis cycle, phenylacetic acid was coupled analogously to a normal Fmoc amino acid. After the end of synthesis, the resin was washed several times with DMF and DCM.

The reaction vessels were removed from the machine and the resin was treated with 2 mL of a mixture of 95% TFA, 2.5% triisopropylsilane, and 2.5% water (v/v). After shaking for 2 h at RT, the cleavage solution was pressed out and the product was precipitated through addition of diethyl ether and centrifuged. The precipitate obtained was washed 2× with diethyl ether and subsequently purified through preparative HPLC; the product-containing fractions were combined and lyophilized (white powder, HPLC: start at 1% B, elution at 22.3 min, MS calcd. 617.79. MS found 309.68 $(M+2H)^{2+}/2$).

Step b) Phac-Arg-Val-Arg-agmatine×3 TFA=Inhibitor 2

48 mg (approx. 0.05 mmol) of Phac-Arg-Val-Arg-NH—$(CH_2)_4$—$NH_2$×3 TFA was treated in a mixture of 1 mL DMF and 1 mL 1M $Na_2CO_3$ solution with 0.15 mmol pyrazole carboxamidine×HCl and 0.2 mmol DIPEA. The assay was stirred at RT for 36 h, the solvent was removed in vacuo, and the product was purified and lyophilized through preparative HPLC (white powder, HPLC: start at 1% B, elution at 23.3 min, MS calcd. 659.8. MS found 660.4 $(M+H)^+$).

PRACTICAL EMBODIMENT 3

Phac-Arg-Val-Arg-4-amidomethyl-N-amidinopiperididex3 TFA=Inhibitor 3

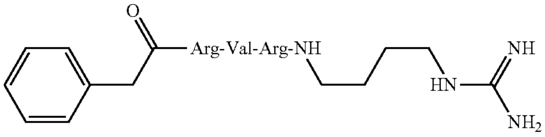

x3 TFA

Step a) N-Boc-(4-aminomethyl)-piperidide

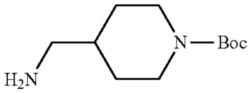

210.4 mg (1 mmol) 4-(Tfa-amidomethyl)-piperidine (Steinmetzer et al., J. Enz. Inhib., 1999, 14, 203-216) was dissolved with 174 μL (1 mmol) DIPEA in 2.5 mL DMF. Under ice cooling, 240 mg (1.1 mmol) $Boc_2O$ were added; the assay was stirred for 1 h under ice cooling and overnight at RT, subsequently, the solvent was removed in vacuo, the residue taken up by EA, washed 3× with 5% $KHSO_4$ solution, and 3× with sat. NaCl solution and dried with $Na_2SO_4$. The solvent was removed in vacuo again (oily residue, which slowly crystallizes at 4 C). The intermediate was dissolved with 3 mL dioxane and 3 mL 1 M NaOH and stirred at 40 C for 3 h. Subsequently, 10 mL water was added and the product was extracted 3× with DCM. The combined DCM phases were dried with $Na_2SO_4$ and, subsequently, the solvent was removed in vacuo (white solid, HPLC: start at 1% B, elution at 26.6 min).

Step b) Phac-Arg-Val-Arg-4-(amidomethyl)-piperididex3 TFA=Inhibitor 3a

The coupling of N-Boc-(4-aminomethyl)-piperidide to Phac-Arg(Pbf)-Val-Arg(Pbf)-OH (obtained from step b of the synthesis practical embodiment 1) was carried out analogously to step c from synthesis practical embodiment 1. After cleavage of the Pbf- and Boc protecting groups remaining on the peptide with a mixture of 95% TFA, 2.5% triisopropylsilane and 2.5% water (v/v) over a time period of 2 h at RT, the intermediate obtained in the cleavage solution was precipitated through addition of diethyl ether and removed by centrifugation; the precipitate was washed 2× with diethyl ether and dried in vacuo. The product was purified through preparative HPLC; the product-containing fractions were combined and lyophilized (white powder, HPLC: start at 1% B, elution at 22.7 min, MS calcd. 643.43. MS found 644.5 $(M+H)^+$.

Step c) Phac-Arg-Val-Arg-4-(amidomethyl)-N-amidinopiperidex3 TFA=Inhibitor 3

The composition of the guanidine group was carried out through reaction of the Phac-Arg-Val-Arg-4-(amidomethyl)-piperidinex3 TFA with pyrazole carboxamidinexHCl and DIPEA analogously to the procedure described in step b of practical embodiment 2. The product was purified and lyophilized through preparative HPLC (white powder, HPLC: start at 1% B, elution at 24.0 min, MS calcd. 685.5. MS found 686.6 $(M+H)^+$.

PRACTICAL EMBODIMENT 4

Further compounds were produced analogously to the synthesis strategy for the inhibitors 2 and 2a. For the first step in the synthesis, the loading of the trityl chloride resin (respectively approx. 100 mg, with an initial loading of 1.5 mmol/g), the corresponding diamine derivative was used, respectively, for example 1,3-diaminopropane for the inhibitors 4 and 4a, or p-diaminoxylene for the compounds 6 and 6a. The structures of the inhibitors are summarized in table 1; all compounds were obtained after preparative HPLC as TFA salts.

TABLE 1

Inhibitors of the general structure Phac-Arg-Val-Arg-P1

| No. of the inhibitor | P1 | HPLC (% B) MS calcd. MS found $(M + H)^+$ |
|---|---|---|
| 4 | 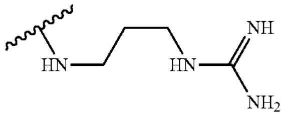 | 23.7<br>645.4<br>646.5 |
| 4a | 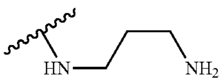 | 23.0<br>603.4<br>604.6 |
| 5 | 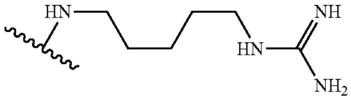 [SMILES: *NCCCCCNC(=N)N] | 25.4<br>673.4<br>674.7 |
| 5a | 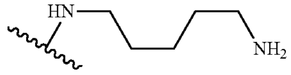 [SMILES: *NCCCCCN] | 23.8<br>631.4<br>632.5 |
| 6 | 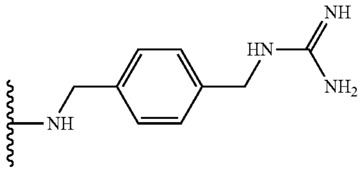 [SMILES: *NCc1ccc(CNC(=N)N)cc1] | 26.3<br>707.4<br>354.7* |
| 6a | 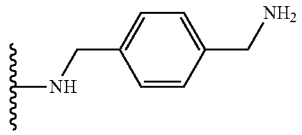 [SMILES: *NCc1ccc(CN)cc1] | 25.2<br>656.4<br>333.7* |
| 7 | 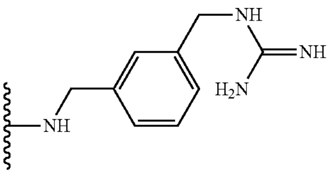 [SMILES: *NCc1cccc(CNC(=N)N)c1] | 26.9<br>707.4<br>708.6 |
| 7a | 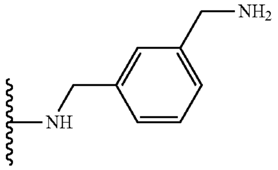 [SMILES: *NCc1cccc(CN)c1] | 25.7<br>656.4<br>333.8* |

*or $(M + 2H)^{2+}/2$

PRACTICAL EMBODIMENT 5

In accordance with the following synthesis strategy, the inhibitors 8-11 were produced according to the standard procedures described above. Fmoc-Lys(Cbz)OH was used as lysine derivative for the solid phase peptide synthesis.

Step a) Synthesis of Phac-Arg(Pbf)-Val-Lys(Cbz)-NH—$(CH_2)_4$—NH-trityl Resin

Synthesis was carried out analogously to step a) in synthesis example 2 using trityl chloride resin and Fmoc-Lys(Cbz) OH as a component, though without cleavage of the protecting groups or the peptide from the resin.

Step b) Phac-Arg-Val-Lys(Cbz)-NH—$(CH_2)_4$—$NH_2$ as 2×TFA Salt=Inhibitor 8

The cleavage of the Pbf protecting group and the peptide from Phac-Arg(Pbf)-Val-Lys(Cbz)-NH—$(CH_2)_4$—NH-trityl resin was carried out with a mixture of 95% TFA, 2.5% triisopropylsilane and 2.5% water (v/v) over a period of 1.5 h at RT, yielding Phac-Arg-Val-Lys(Cbz)-NH—$(CH_2)_4$—$NH_2$ as 2×TFA salt. The product was precipitated with diethyl ether, washed 2× with diethyl ether and purified through preparative HPLC (inhibitor 8, white lyophilized powder following preparative HPLC, HPLC: start at 1% B, elution at 36.2 min, MS calcd. 723.4. MS found 724.6 $(M+H)^+$).

Step c) Phac-Arg-Val-Lys(Cbz)-agmatine×2 TFA=Inhibitor 9

Phac-Arg-Val-Lys(Cbz)-NH—$(CH_2)_4$—$NH_2$×2 TFA (inhibitor 8) was reacted in DMF with 3-fold excess of pyrazole carboxamidine×HCl and 4-fold excess of DIPEA. The product was purified through preparative HPLC (inhibitor 9, white lyophilized powder following preparative HPLC, HPLC: start at 1% B, elution at 36.8 min, MS calcd. 765.5. MS found 776.5 $(M+H)^+$.

Step d) Phac-Arg-Val-Lys-agmatine×3 TFA=Inhibitor 10

Phac-Arg-Val-Lys(Cbz)-agmatine×2 TFA (inhibitor 9) was hydrogenated with $H_2$ and 10 mass percent Pd/C as a catalyst in 90% acetic acid for 12 h at RT and the product was purified through preparative HPLC (inhibitor 10, white lyophilized powder following preparative HPLC, HPLC: start at 1%, elution at 23.1 min, MS calcd. 631.4. MS found 316.7 $(M+2H)^{2+}/2$).

Step e) Phac-Arg-Val-hArg-agmatine×3 TFA=Inhibitor 11

Phac-Arg-Val-Lys-agmatine×3 TFA (inhibitor 10) was reacted with a mixture of the same volumes of DMF and 1M $Na_2CO_3$ solution with approx. 3 eq. pyrazole carboxamidine× HCl and 4 eq. DIPEA analogously to step b) of practical embodiment 2 (inhibitor 11, white lyophilized powder following preparative HPLC, HPLC: start at 1% B, elution at 24.3 min, MS calcd. 673.4. MS found 674.4 $(M+H)^+$.

PRACTICAL EMBODIMENT 6

Enzyme Kinetic Studies to Determine the Inhibitory Effect on Furin

The determination of the inhibitory effect was carried out with a fluorescence plate reader Safire$^2$ from the Tecan company ($\lambda_{Ex}$=380 nm, $\lambda_{Em}$=460 nm) and Pyr-Arg-Thr-Lys-Arg-AMC (Bachem, No: I-1650) as the substrate. Recombinantly produced human furin (Kacprzak, M. M. et al., J. Biol. Chem., 2004, 279, 36788-36794) was used in the measurement assay in a concentration of approx. 0.95 nM.

To determine the inhibition constants, the inhibitor concentration was varied at least over the range of an order of magnitude at a constant substrate concentration (12.5 μM in the assay), and, respectively, the steady-state velocity was determined. $K_m$ and $V_{max}$ were determined by means of v/S characteristics parallel to each inhibitor measurement. The calculation of $K_i$ values was carried out through adjustment of the determined velocities as a function of the inhibitor concentration to the velocity equation for competitively, reversibly-binding inhibitors:

$$v = \frac{V_{max} \cdot [S]}{K_m \cdot \left(1 + \frac{[I]}{K_i}\right) + [S]}$$

TABLE 2

$K_i$ values (μM) of chosen inhibitors for the inhibition of furin

| Inhibitor | $K_i$ value (μM) |
|---|---|
| 1 | 0.0014 |
| 2 | 0.077 |
| 2a | 25 |
| 3 | 0.068 |
| 3a | 10 |
| 4 | 0.097 |
| 4a | 1.3 |
| 5 | 1.6 |
| 10 | 0.049 |
| 11 | 0.047 |

PRACTICAL EMBODIMENT 7

Inhibition of the Proteolytic Cleavage of the Hemagglutinin (HA) of Avian Influenza Virus (FPV)

The HA surface protein of the avian influenza virus (which belongs to the highly pathogenic influenza viruses of the subtypes H5 and H7) is produced as the precursor protein HA0. HA0 is hydrolyzed at a multibasic cleavage site by the protease furin, or by a furin-like enzyme; these proteases occur in practically every cell. Through this, the subunit HA1 and the membrane-bound HA2 are formed. This cleavage is the prerequisite for the formation of infectious viruses, in order for them to be able to fuse with the endosome membrane of the target cell. If the proteolytic cleavage of HA into HA1 and HA2 is inhibited, the merging, and thus the further replication of the viruses as well, are inhibited. Cells infected by avian influenza viruses were treated with different concentrations of the inhibitor 1 and a previously described control inhibitor (decanoyl-Arg-Val-Lys-Arg-chloromethyl ketone, Hallenberger, S. et al., Nature, 1992, 360, 358-361) and the cleavage of HA was examined.

In FIG. 1A, the inhibition of the HA cleavage of the avian influenza virus by different concentrations of inhibitor 1 and the reference inhibitors Dec-Arg-Val-Lys-Arg-CMK are represented.

The gel figure A shows, in this, the results of the following experiment: confluent MDCK cell cultures were infected with influenza virus A/FPV/Rostock/34 (H7N1) at a MOI of 10 per cell. 16 hours after infection, the cells were lysed and the inhibition of the HA cleavage (PSKKRKKR↓GLFG) depending on the inhibitor concentration was examined by means of SDS-PAGE and Western blotting. The viral proteins were detected immunochemically with a rabbit anti-FPV-serum using the ECL-Test from the Pierce company: HA0 (82 kDa), nucleoprotein NP (56 kDa) and HA1 (~50 kDa), wherein HA2 (32 kDa) is not detectable with the antiserum used.

The statistical evaluation is represented in illustration FIG. 1B. The quantification of the inhibition of the HA cleavage is recognizable. Respectively, three independent experiments were carried out for both inhibitors; quantification was carried out by means of a second monoclonal antibody, which is marked with an IR dye and is detectable with the LI-COR Odyssey Image-System. The maximal amount of HA0 at 50 μM Dec-Arg-Val-Lys-Arg-CMK was set as 100% inhibition of the cleavage. The intensities of the HA0 bands at the different inhibitor concentrations were normalized by means of the intensity of the bands for the nucleoprotein (NP at 56 kDa).

PRACTICAL EMBODIMENT 8

Inhibitor of Multicyclic Replication of FPV in the Presence of the Inhibitor 1

In a further experiment, the long-term effects of the inhibitor 1 on the multicyclic replication of the avian influenza virus (FPV) was examined (for methods, see Garten et al., *Virology* 1989, 172, 25-31). MDCK cells were infected with FPV at low multiplicity of infection (MOI) of $10^{-5}$ and incubated in the presence of a concentration of 25 μM of inhibitor 1 for a time period of 72 h. As a control, the infected cells were incubated without inhibitor. The replication of FPV was examined through virus titration into the cell culture supernatants with a standard hemagglutination test (Garten et al., *Virology* 1989, 172, 25-31, FIG. 3). Virus release in the group treated with the inhibitor is delayed by about 24 h in relation to the untreated control group. The delayed virus replication in the presence of the inhibitor also makes it clear that the vitality of the cells is not influenced by the inhibitor.

FIG. 2 shows the multicyclic replication of FPV in cell culture in the presence (white bars) of inhibitor 1 (25 μM) and without inhibitor (black bars). MDCK cell cultures were incubated with the influenza strain A/FPV/Rostock/34 (H7N1) at a MOI of $10^{-5}$ per cell at 37° C. At the indicated time periods (10, 18, 32, 48, 60, and 72 h after infection), the viral amount in the medium were determined with the hemagglutination test. The average values of four independent experiments were shown.

PRACTICAL EMBODIMENT 9

According to the methods described above, the $K_i$ values for the inhibition of furin were also determined for the synthesized inhibitors represented in table 3.

TABLE 3

Structures of further synthesized inhibitors and $K_i$ values for the inhibition of furin for selected inhibitors.

| No. | Structure | HPLC min | MS calcd. | MS found | $K_i$ (μM) |
|---|---|---|---|---|---|
| 12 | 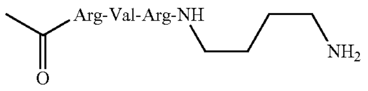 | 13.64 | 541.69 | 542.21 $(M + H)^+$ | 41.21 |
| 13 | 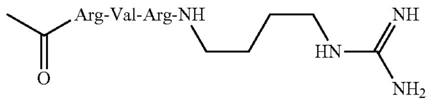 | 15.86 | 583.73 | 195.45 $(M + 3H)^{3+}$ | 0.315 |
| 14 | 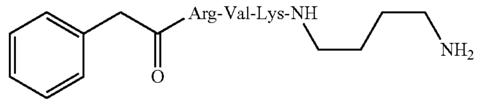 | 21.76 | 589.41 | 590.41 $(M + H)^+$ | 5.41 |
| 15 | 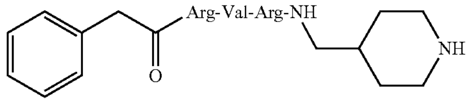 | 23.12 | 643.43 | 644.4 $(M + H)^+$ | 9.708 |
| 16 | 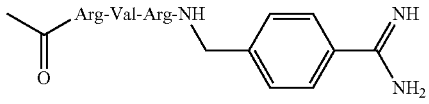 | 16.83 | 602.38 | 201.84 $(M + 3H)^{3+}$ | 0.002 |
| 17 | 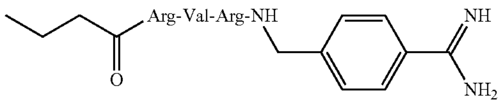 | 20.40 | 630.41 | 316.26 $(M + 2H)^{2+}$ | 0.00077 |
| 18 | 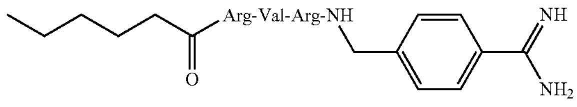 | 26.29 | 658.44 | 330.3 $(M + 2H)^{2+}$ | 0.00082 |

TABLE 3-continued
Structures of further synthesized inhibitors and $K_i$ values for the inhibition of furin for selected inhibitors.
| No. | Structure | HPLC min | MS calcd. | MS found | $K_i$ (μM) |
|---|---|---|---|---|---|
| 19 | 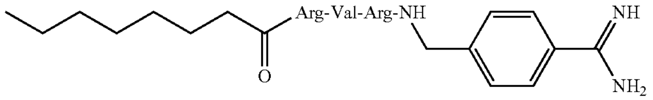 | 32.73 | 686.47 | 344.29 $(M + 2H)^{2+}$ | 0.00082 |
| 20 | 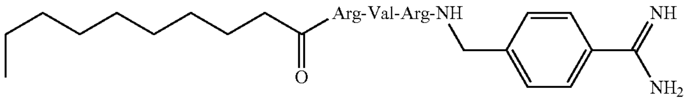 | 38.78 | 714.5 | 239.26 $(M + 3H)^{3+}$ | 0.0024 |
| 21 | 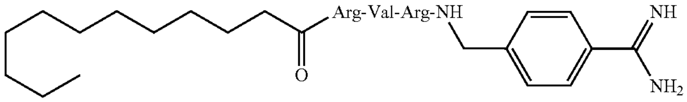 | 15.16 | 742.53 | 372.32 $(M + H)^{+}$ | 0.0067 |
| 22 | 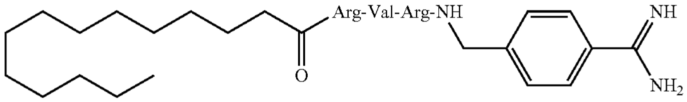 | 20.40* | 770.56 | 386.37 $(M + 2H)^{2+}$ | 0.0569 |
| 23 | 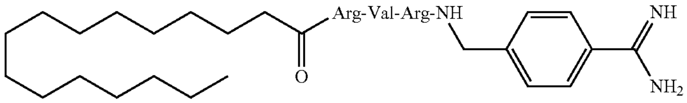 | 25.38* | 798.6 | 267.28 $(M + 3H)^{3+}$ | 0.024 |
| 24 | 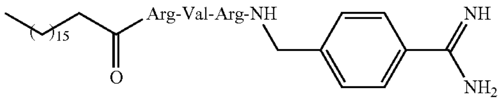 | 30.66* | 826.63 | 276.63 $(M + 3H)^{3+}$ | 2.46 |
| 25 | 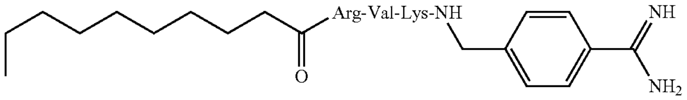 | 38.12 | 686.5 | 344.29 $(M + 2H)^{2+}$ | 0.0033 |
| 26 | 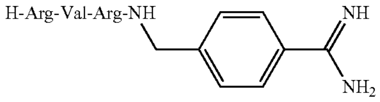 | 15.12 | 560.37 | 561.3 $(M + H)^{+}$ | 0.0076 |
| 27 | 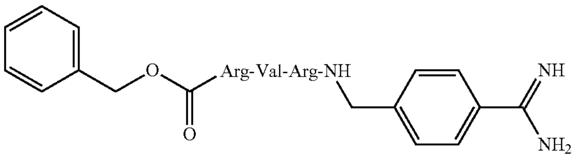 | 27.78 | 694.4 | 232.57 $(M + 3H)^{3+}$ | 0.0024 |
| 28 | 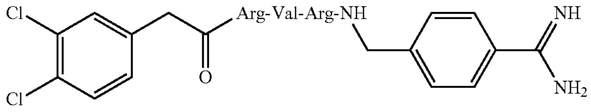 | 31.72 | 746.33 | 374.24 $(M + 2H)^{2+}$ | 0.0012 |
| 29 | 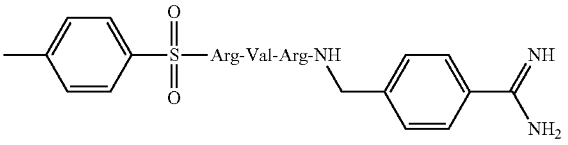 | 27.02 | 714.37 | 358.25 $(M + 2H)^{2+}$ | 0.0048 |

TABLE 3-continued
Structures of further synthesized inhibitors and $K_i$ values for the inhibition of furin for selected inhibitors.
| No. | Structure | HPLC min | MS calcd. | MS found | $K_i$ ( μM) |
|---|---|---|---|---|---|
| 30 | 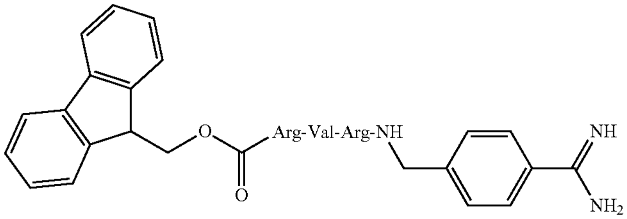 | 36.80 | 782.43 | 261.93 $(M + 3H)^{3+}$ | 0.011 |
| 31 | 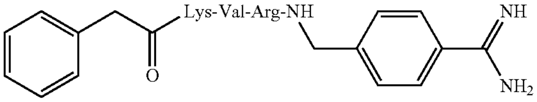 | 27.00 | 650.4 | 326.3 $(M + 2H)^{2+}$ | 0.285 |
| 32 | 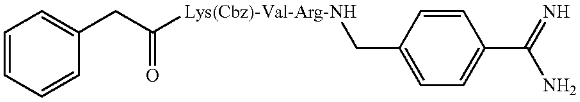 | 39.49 | 784.44 | 393.26 $(M + 2H)^{2+}$ | 0.7 |
| 33 | 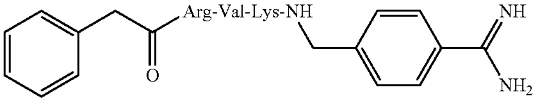 | 23.98 | 650.4 | 326.22 $(M + 2H)^{2+}$ | 0.0015 |
| 34 | 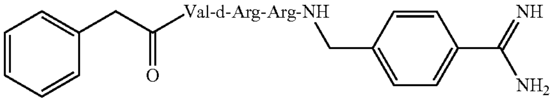 | 25.95 | 678.41 | 227.24 $(M + 3H)^{3+}$ | 7.34 |
| 35 | 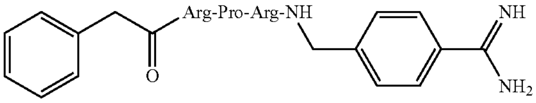 | 22.77 | 676.39 | 226.5 $(M + 3H)^{3+}$ | 0.031 |
| 36 | 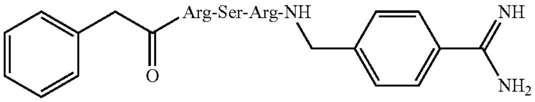 | 20.70 | 666.37 | 334.26 $(M + H)^{+}$ | 0.015 |
| 37 | 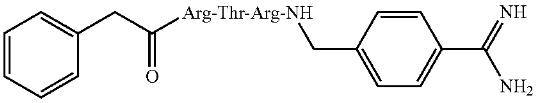 | 21.40 | 680.39 | 341.26 $(M + H)^{+}$ | 0.005 |
| 38 | 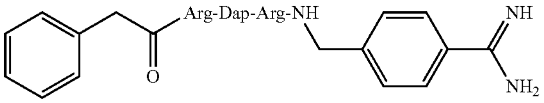 | 19.87 | 665.39 | 666.22 $(M + H)^{+}$ | 0.0028 |
| 39 | 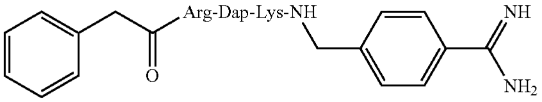 | 19.06 | 637.38 | 638.25 $(M + H)^{+}$ | 0.0037 |
| 40 | 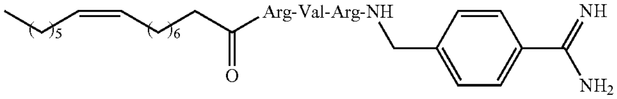 | 54.50 | 796.6 | 399.8 $(M + 2H)^{2+}$ | n.d. |
| 41 | 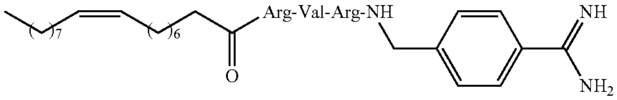 | 58.20 | 824.6 | 413.63 $(M + 2H)^{2+}$ | n.d. |

TABLE 3-continued
Structures of further synthesized inhibitors and $K_i$ values for the inhibition of furin for selected inhibitors.
| No. | Structure | HPLC min | MS calcd. | MS found | $K_i$ (μM) |
|---|---|---|---|---|---|
| 42 | 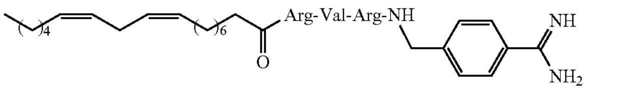 | 55.10 | 822.6 | 412.56 $(M + 2H)^{2+}$ | n.d. |
| 43 | 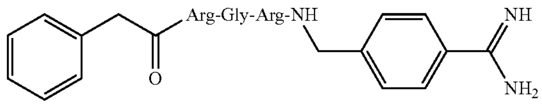 | 21.40 | 636.4 | 319.32 $(M + 2H)^{2+}$ | 0.042 |
| 44 | 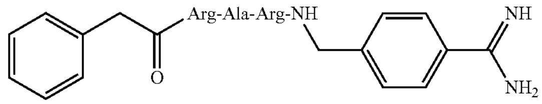 | 21.80 | 650.4 | 326.35 $(M + 2H)^{2+}$ | 0.019 |
| 45 | 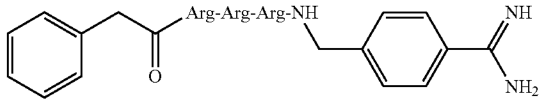 | 21.50 | 735.4 | 368.83 $(M + 2H)^{2+}$ | 0.0026 |
| 46 | 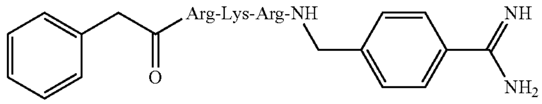 | 19.90 | 707.4 | 354.83 $(M + 2H)^{2+}$ | n.d. |
| 47 | 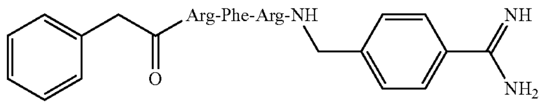 | 29.90 | 726.4 | 364.32 $(M + 2H)^{2+}$ | n.d. |
| 48 | 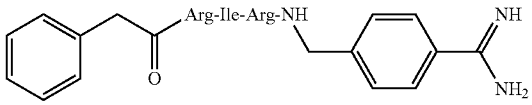 | 27.10 | 692.4 | 347.34 $(M + 2H)^{2+}$ | n.d. |
| 49 | 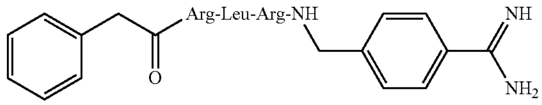 | 27.50 | 692.4 | 347.32 $(M + 2H)^{2+}$ | n.d. |
| 50 | 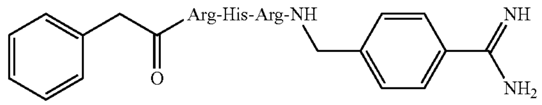 | 20.20 | 716.4 | 359.29 $(M + 2H)^{2+}$ | n.d. |
| 51 | 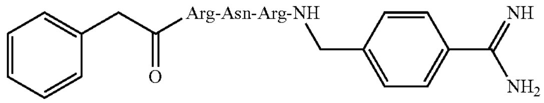 | 20.60 | 693.4 | 347.9 $(M + 2H)^{2+}$ | n.d. |
| 52 | 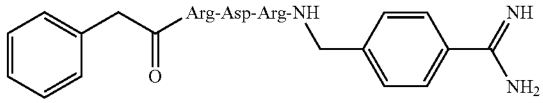 | 21.00 | 694.4 | 348.3 $(M + 2H)^{2+}$ | n.d. |
| 53 | 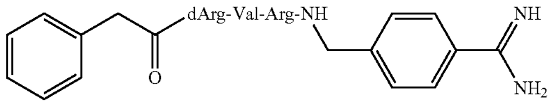 | 22.90 | 678.4 | 340.33 $(M + 2H)^{2+}$ | n.d. |
| 54 | 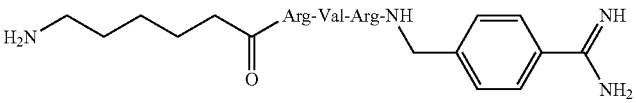 | 16.50 | 673.5 | 337.88 $(M + 2H)^{2+}$ | n.d. |

TABLE 3-continued

Structures of further synthesized inhibitors and $K_i$ values for the inhibition of furin for selected inhibitors.

| No. | Structure | HPLC min | MS calcd. | MS found | $K_i$ (μM) |
|---|---|---|---|---|---|
| 55 | 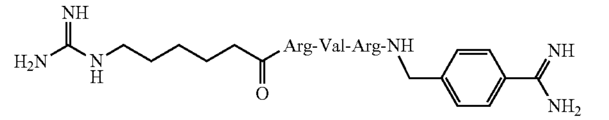 | 19.30 | 715.5 | 358.88 $(M + 2H)^{2+}$ | n.d. |
| 56 | 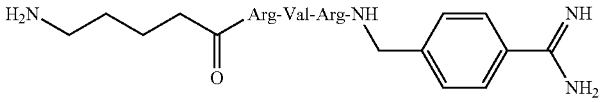 | 15.70 | 659.4 | 330.91 $(M + 2H)^{2+}$ | n.d. |
| 57 | 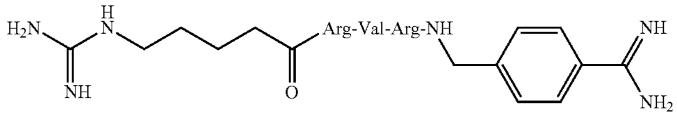 | 17.30 | 701.5 | 351.88 $(M + 2H)^{2+}$ | n.d. |
| 58 | 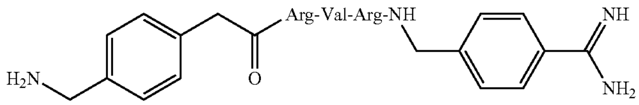 | 18.10 | 707.4 | 354.89 $(M + 2H)^{2+}$ | n.d. |
| 59 | 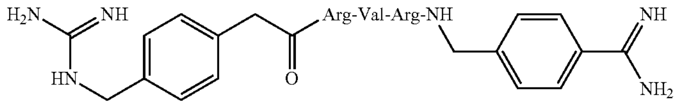 | 19.70 | 749.5 | 375.91 $(M + 2H)^{2+}$ | n.d. |
| 60[§] | 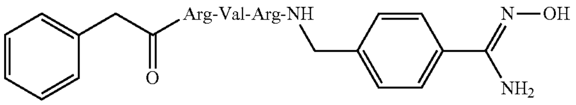 | 32.10 | 694.4 | 348.22 $(M + 2H)^{2+}$ | n.d. |
| 61[#] | 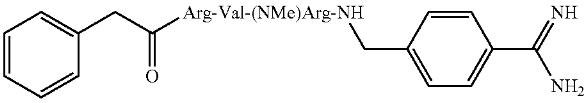 | 30.40 | 692.4 | 347.37 $(M + 2H)^{2+}$ | n.d. |
| 62[#] | 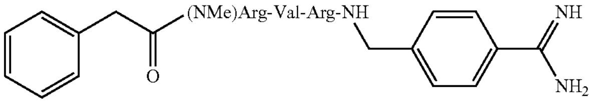 | 30.40 | 692.4 | 347.38 $(M + 2H)^{2+}$ | n.d. |

[*] Start of the HPLC at 30% B; for all other compounds, start of the HPLC at 1% B.

[§] This compound is a hydroxyamidino prodrug of inhibitor 1.

[#] These compounds were produced using Fmoc—N(methyl)Arg(Mtr)—OH (Bachem, Schweiz, order number B-2840) using PyBOP and PyBrOP as a coupling reagent according to previously described methods (Steinmetzer et al., Biol. Chem. 381, 603-610, 2000).

(n.d. = not determined)

The invention claimed is:

1. A compound according to formula (I)

P5-P4-P3-P2-P1 (I)

wherein P5-P4-P3-P2-P1 is a tetrapeptide derivative and wherein P1 is a decarboxylated arginine mimetic, wherein the compounds, including their salts, are selected from the structures:

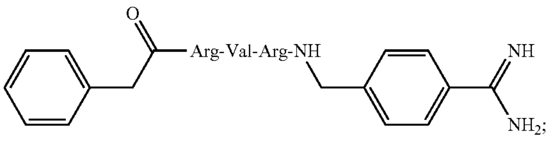

-continued

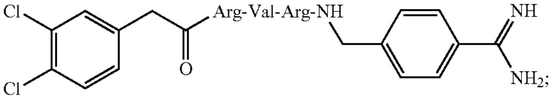

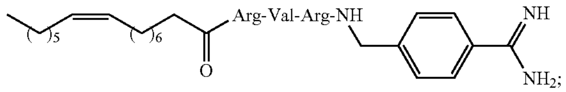

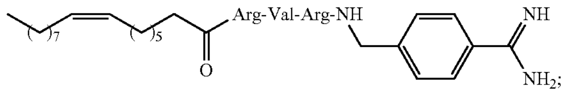

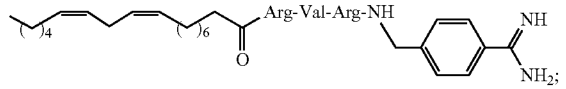

-continued

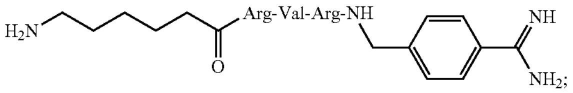

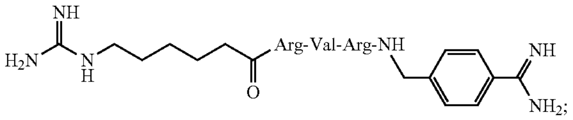

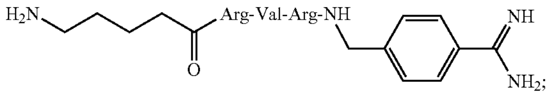

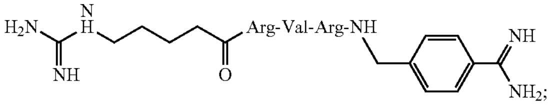

-continued

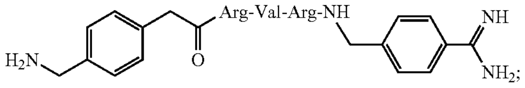

and

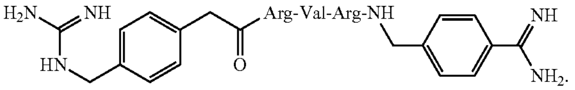

2. A pharmaceutical composition comprising at least one compound according to claim 1.

3. The pharmaceutical composition according to claim 2, wherein the pharmaceutical composition is in the form of a tablet, dragee, capsule, pellet, suppositorium, a solution, eye drops, nose drops or ear drops, a juice, an emulsion or suspension, a globule, a stylus, an aerosol, an aerosol spray, a powder, a paste, a cream or an ointment.

* * * * *